(12) United States Patent
Mole

(10) Patent No.: US 9,005,531 B2
(45) Date of Patent: Apr. 14, 2015

(54) AIR DECONTAMINATION DEVICE AND METHOD

(75) Inventor: Alan Mole, Pershore (GB)

(73) Assignee: Tri-Air Developments Limited, London (GB)

(*) Notice: Subject to any disclaimer, the term of this patent is extended or adjusted under 35 U.S.C. 154(b) by 787 days.

(21) Appl. No.: 13/259,815

(22) PCT Filed: Feb. 26, 2010

(86) PCT No.: PCT/GB2010/000346
§ 371 (c)(1),
(2), (4) Date: Dec. 9, 2011

(87) PCT Pub. No.: WO2010/109160
PCT Pub. Date: Sep. 30, 2010

(65) Prior Publication Data
US 2012/0093691 A1    Apr. 19, 2012

(30) Foreign Application Priority Data
Mar. 24, 2009    (GB) ................................. 0904978.4

(51) Int. Cl.
*A62B 7/08* (2006.01)
*A61L 9/22* (2006.01)
(Continued)

(52) U.S. Cl.
CPC ... *A61L 9/22* (2013.01); *A61L 2/14* (2013.01); *B01D 53/323* (2013.01); *B01D 53/885* (2013.01); *B01D 2255/802* (2013.01);
(Continued)

(58) Field of Classification Search
CPC ...... A61L 9/20; F24F 3/16; F24F 2003/1664; F24F 2003/1667
USPC ........................... 422/120, 121, 122, 123, 124
See application file for complete search history.

(56) References Cited

U.S. PATENT DOCUMENTS 5,961,920 A * 10/1999 Soremark ......................... 422/24
5,993,738 A * 11/1999 Goswani .......................... 422/22
(Continued)

FOREIGN PATENT DOCUMENTS

DE    35 15 508 C1    10/1986
EP    1799330 A1    6/2007
(Continued)

OTHER PUBLICATIONS

Search Report for International Patent Application No. PCT/GB2010/000346; Jul. 19, 2010.
(Continued)

*Primary Examiner* — Regina M Yoo
(74) *Attorney, Agent, or Firm* — Barnes & Thornburg LLP

(57) ABSTRACT

An apparatus for the decontamination of air, the apparatus comprising a housing (1) having an air inlet (4) and an air outlet (6) with an air passage (2) there between, means (20) for directing a stream of air through the housing, the housing containing a non-thermal plasma cell (30), an ultraviolet emitting device (40) and an ozone depletion catalyst (42), the non-thermal plasma comprising an anode (32), a dielectric (32) and a cathode (33), the cathode being in the form of a meshed enclosure which surrounds the ultraviolet emitting device and ozone depletion catalyst to form a reaction chamber and Faraday cage. The non-thermal plasma cell may also be provided as a columnar cell for forming an array of cells and the dielectric may comprise water droplets to improve the efficiency of the device.

7 Claims, 6 Drawing Sheets

(51) Int. Cl.
*A61L 2/14* (2006.01)
*B01D 53/32* (2006.01)
*B01D 53/88* (2006.01)
*B03C 3/016* (2006.01)
*B03C 3/09* (2006.01)
*B03C 3/16* (2006.01)
*B03C 3/36* (2006.01)
*B03C 3/64* (2006.01)
*F24F 3/16* (2006.01)
*H05H 1/24* (2006.01)

(52) U.S. Cl.
CPC ....... *B01D2257/106* (2013.01); *B01D 2257/90* (2013.01); *B01D 2257/91* (2013.01); *B01D 2259/4508* (2013.01); *B01D 2259/804* (2013.01); *B01D 2259/806* (2013.01); *B03C 3/016* (2013.01); *B03C 3/09* (2013.01); *B03C 3/16* (2013.01); *B03C 3/366* (2013.01); *B03C 3/64* (2013.01); *F24F 3/16* (2013.01); *F24F 2003/1667* (2013.01); *F24F 2003/1682* (2013.01); *H05H 1/24* (2013.01)

(56) References Cited

U.S. PATENT DOCUMENTS

| | | | |
|---|---|---|---|
| 6,358,478 B1 * | 3/2002 | Soremark | 422/121 |
| 6,500,387 B1 * | 12/2002 | Bigelow | 422/24 |
| 6,589,489 B2 * | 7/2003 | Morrow et al. | 422/186.3 |
| 6,620,385 B2 * | 9/2003 | Fujii | 422/186.3 |
| 2006/0188387 A1 * | 8/2006 | Goswami | 422/4 |
| 2007/0020159 A1 | 1/2007 | Tsui | |
| 2007/0137486 A1 | 6/2007 | Bergeron et al. | |
| 2007/0217944 A1 * | 9/2007 | Potember et al. | 422/4 |
| 2007/0253860 A1 * | 11/2007 | Schroder | 422/4 |
| 2008/0170971 A1 | 7/2008 | Bergeron et al. | |
| 2008/0193326 A1 * | 8/2008 | Mole | 422/2 |
| 2010/0178196 A1 * | 7/2010 | Garner | 422/4 |

FOREIGN PATENT DOCUMENTS

| | | | | |
|---|---|---|---|---|
| EP | 2019464 A1 | 1/2009 | | |
| JP | 2008-504094 A2 | 2/2008 | | |
| JP | 2009-519819 A | 5/2009 | | |
| WO | 9912637 A1 | 3/1999 | | |
| WO | WO 2006003382 A1 * | 1/2006 | ............ | B01D 53/32 |
| WO | 2007051912 A1 | 5/2007 | | |
| WO | 2009002295 A1 | 12/2008 | | |

OTHER PUBLICATIONS

Notification of Reasons for Rejection for Application No. 2012-501365, mailed Aug. 6, 2013.
Great Britain Search Report for Application No. GB0904978.4, dated Jul. 23, 2009.

* cited by examiner

AIR DECONTAMINATION DEVICE AND METHOD

The present invention relates to an improved device for the decontamination of air and surfaces.

Air purity and being able to consistently remove contaminants entrained in the air is extremely important, especially in supposedly sterile or hygienic environments, such as hospitals and kitchens. It is also beneficial having decontaminated air in doctors' surgeries, and workplace environments making it more difficult for germs and disease to spread.

In addition to microbiological contaminants, chemical gases or vapours can present a serious hazard, either as a by-product of industrial processing or as a malicious attack through terrorism or chemical warfare.

The Applicant's earlier patent (EP1799330) provides an efficient method and active component is the hydroxyl radical (OH) which is second only to fluorine as an oxidising species but has the advantage of having no significant toxicity to higher organisms, while being lethal to pathogenic bacteria and viruses.

The hydroxyl radical is present in high concentrations in tropospheric air due to the presence of related trosposheric components, principally ozone and unsaturated hydrocarbons. These components are missing or much reduced in indoor air thus causing the concentration of hydroxyl radicals to be correspondingly low. The Applicant's earlier invention re-creates tropospheric conditions indoors to increase the population of hydroxyl radicals which acts to reduce the level of harmful contaminants, particularly pathogenic bacterial and viruses, within an indoor or enclosed environment.

Whilst the process and device of the Applicant's earlier disclosure has been found to be highly effective at re-creating an outdoor environment indoors, there is always room for enhancing its efficiency and reliability.

It is an aim of the present invention to provide an improved apparatus for the decontamination of air and surfaces.

According to a first aspect of the present invention, there is provided an apparatus for the decontamination of air, the apparatus comprising a housing having an air inlet and an air outlet with an air passage therebetween, means for directing a stream of air through the housing, the housing containing a non-thermal plasma cell, an ultraviolet emitting device and an ozone depletion catalyst, the non-thermal plasma comprising an anode, a dielectric and a cathode, the cathode being in the form of a meshed enclosure which surrounds the ultraviolet emitting device and ozone depletion catalyst to form a reaction chamber and Faraday cage.

Preferably, a hydrocarbon emitter is provided within the housing downstream of the rection chamber, preferably adjacent or in the vicinity of the outlet. Alternatively or additionally, a water droplet emitter, preferably in the form of an atomiser, may be provided to deliver an ultra-fine spray of de-ionised water into the reaction chamber. It is to be appreciated that the hydrocarbon emitter and water droplet emitter would be connected to suitable source reservoirs having appropriate delivery mechanisms.

The housing may also include means for delivering microwaves of a certain wavelength to the reaction chamber, such as a magnetron. This removes the need of a separate power circuit to the ultraviolet emitting device.

A fan or impellor is preferably provided at or in the vicinity of the inlet for directing air through the passage.

The anode preferably comprises a reticulated conductive or semi-conductive element, such as a carbon and aluminium composite. The dielectric may be any suitable non-conducting material or insulator. In one preferred embodiment, the dielectric comprises activated alumina pellets. The material may be coated with a catalytic material. In an alternative embodiment of the invention, the dielectric comprises deionised water droplets or vapour.

To this end there is provided an apparatus for the decontamination of air, the apparatus comprising a housing having an air inlet and an air outlet with an air passage therebetween, means for directing a stream of air through the housing, the housing containing a non-thermal plasma cell, an ultraviolet emitting device and an ozone depletion catalyst, the non-thermal plasma comprising an anode, a dielectric and a cathode, the dielectric comprising deionised water droplets or vapour.

The cathode preferably comprises a porous mesh of conducting material that is formed into a cage-like structure for surrounding the UV emitting device and catalyst. Preferably, the cathode also houses a microwave emitter for delivering microwaves of a certain wavelength to excite the UV emitting device. Preferably, the microwave emitter generates wavelengths in the Radio Frequency range 2200-2600 MHz, such as 2450 MHz.

It is preferably for the catalyst to surround the UV emitting device. Preferably, the UV emitting device is tubular and surrounded by a mesh of an ozone-catalysing device. Preferably, the coating on the mesh forms the catalyst.

Appropriate supporting members may be provided between the cage and the UV emitter/catalyst and/or between the emitter and the catalyst. The supporting elements are preferably coated with a material that acts as a catalyst to the reaction and may be profiled to impart a swirling motion to the air passing through the reaction chamber.

The plasma cell for the apparatus may be provided in alternate forms to increase the efficiency of the device. The replacement of the dielectric with fine deionised water droplets, preferably with a minimum resistance of typically 18 M$\Omega$/cm, minimises back pressure on the air delivery system reducing energy requirements and noise and further, increases the yield of OH. radicals.

To this end, a third aspect of the present invention provides a non-thermal plasma cell for an apparatus for the decontamination of air, the plasma cell comprising an anode and a cathode with a dielectric therebetween, the dielectric comprising deionised water droplets or vapour.

It is to be appreciated that the cell should have a suitable power supply to the anode. Preferably, the cathode is earthed.

Preferably, the cathode of the non-thermal plasma cell according to the third aspect of the invention comprises a hollow tube of conducting material. The anode is preferably provided within the tube spaced apart from the walls forming the cathode to provide a dielectric space therebetween. More preferably, the anode is fixed centrally within the tube.

Preferably, a water reservoir is connected to the dielectric space. An air inlet is also provided for delivering air to the reservoir. An atomiser may be provided for providing a fine mist of water droplets within the space. Appropriate air movement means, such as a fan, is preferably provided to propel the water droplets into the dielectric space.

The plasma cell may also be provided with a further air inlet for delivering air from an alternative source, such as air from the surrounding environment, to the dielectric space. Again air movement means may be provided to assist this delivery.

It is to be appreciated that a plasma cell according to the third aspect of the present invention may be provided within an air decontamination device comprising a housing having an air inlet and an air outlet with an air passage therebetween, means for directing a stream of air through the housing, the housing containing the non-thermal plasma cell, an ultraviolet emitting device and an ozone depletion catalyst.

According to a fourth aspect of the present invention there is provided a non thermal plasma cell comprising a columnar cell having a substantially central anode surrounded by a cathode with dielectric therebetween.

Preferably, the cathode forms the wall of the column. The column may be any three-dimensional shape but preferably is cylindrical. Alternatively, the column may be a polygon having at least five sides. Preferably, the polygon is a regular polygon.

It is preferable for the cathode to be comprised of a mesh of conducting material that surrounds the dielectric provided between the anode and cathode. Any appropriate non-conducting material may be used for the dielectric, but preferable materials are activated alumina pellets or deionised water droplets.

A suitable power supply should be provided to the anode and the cathode is preferably earthed.

The individual columnar cells may be arranged into an array to form an enlarged non-thermal plasma body. The array may be incorporated into an air decontamination device to provide a plasma field for the passage of air to be decontaminated that has reduced back pressure against the flow of air.

To this end, a fifth aspect of the present invention provides an array of non-thermal plasma cells, the array comprising a plurality of non-thermal plasma cells. The array of non-thermal plasma cells may be provided within an air decontamination device comprising a housing having an air inlet and an air outlet with an air passage therebetween, means for directing a stream of air through the housing, the housing containing the array of non-thermal plasma cells, an ultraviolet emitting device and an ozone depletion catalyst.

The array preferably comprises multiple rows of the columnar cells according to a fourth aspect of the present invention, adjacent rows being staggered with respect to one another. The individual cells making up the array may be sequentially switched at a frequency sufficient to maintain a non-thermal plasma in the individual cells, even though the power supplying that cell is momentarily absent. Such sequential switching may be obtained by any suitable means known in the art, such as using proprietary automotive distribution technology, electro-mechanical or solid-state.

It is preferable for an outer wall housing the array of plasma cells to be insulated, for example with a laminated structure, such as silicone rubber.

Optionally, baffles may be provided at locations within or surrounding the array to aid air flow therethrough.

The present invention will now be more particularly described, by way of example, with reference to the accompanying drawings, in which:

FIG. 3a is schematic diagram of a non-thermal plasma cell according to another aspect of the present invention;

FIG. 3b is a transverse cross-section through A-A shown in FIG. 3a;

Figure 1:
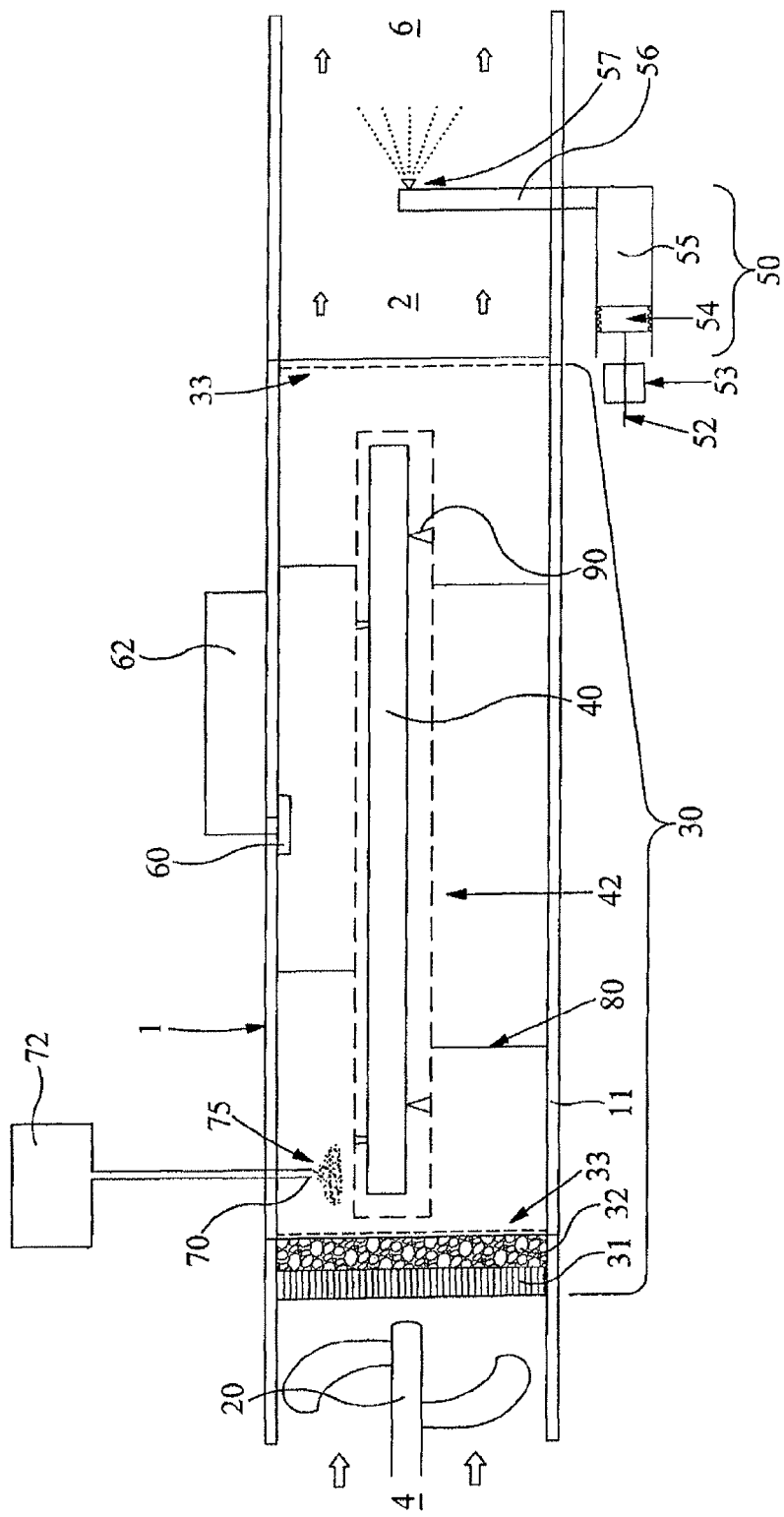
FIG. 1 shows a longitudinal cross-sectional view of an air decontamination device, in accordance with a first aspect of the invention.
Figure 2:
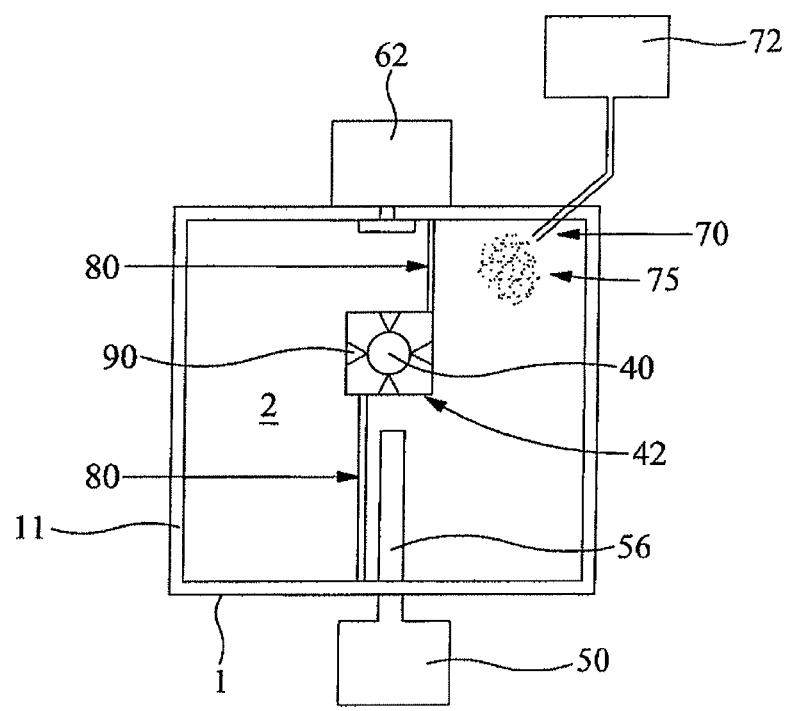
FIG. 2 is a transverse cross-sectional view through the device shown in FIG. 1.

Referring to FIGS. 1 and 2 of the accompanying drawings, there is shown an air decontamination device according to a first aspect of the present invention which comprises a housing 1 having a flow passage 2, an air inlet 4 to the flow passage 2 and an air outlet 6 exiting from the passage 2. An air stream generator in the form of a fan or impeller 20 is provided for forcing air through the housing 1. As a safety measure, a grill (not shown) may be provided across the air inlet 4 to prevent accidental access to the impellor while in operation. A power supply (not shown) may be a proprietary product but should be capable of supplying a power of 12-25 Kv at between 10-30 KHz.

A non-thermal plasma filter, identified collectively as 30 in FIG. 1, comprises an anode or high voltage electrode 31, a dielectric 32 and a porous mesh 33 in the form of a cage which functions not only as the cathode but also the end of the reaction chamber.

The anode 31 comprises reticulated (three dimensionally porous) conductive elements, in this case being aluminium and carbon composite. However, any rigid reticulated conductive or semi-conductive material could be used. The dielectric 32 is activated alumina pellets, nominally 3 to 4 millimeters in diameter. However, again, the dielectric 32 could be any suitable material to suit varying applications and specific requirements. The dielectric may consist of a non-conductive matrix of porous foam and/or may be coated with a catalytic material. The catalyst may be selected to target the destruction of a specific compound or group of compounds. The cathode 33 comprises a porous mesh of conducting material, such as an expanded stainless steel mesh, which substantially follows the internal contours of the housing to form a hollow cage. This is able to act as a "Faraday Cage" serving, to block out external static electrical fields and allow only radiation of a certain wavelength to enter the interior of the cage. The cage may have an internal coating of UV catalysing material, in this case Anatase form Titanium dioxide.

The cage formed by the cathode 33 houses an ultraviolet radiation emitting device 40 comprising an ultraviolet tube surrounded by a photocatalytic element 42. The cage also incorporates a microwave emitter 60 connected to a magnetron 62. Additionally, a discharge nozzle or orifice 70 is provided in the cage which is connected to a deionised water reservoir 72 for delivering a fine spray of deionised water 75.

A hydrocarbon emitter, shown collectively as 50 in FIG. 1, is provided downstream of the Faraday cage adjacent to or in the vicinity of the exit 6 from the housing 1. The hydrocarbon emitter 50 includes a rechargeable hydrocarbon reservoir 55 containing a liquid aromatic hydrocarbon, for example an olefin such as a Terpene. The delivery system of the hydrocarbon emitter 50 comprises a threaded bar 52 which passes through to a stepper motor 53. The bar pushes a piston 54 through the reservoir 55 to force the hydrocarbon through a tube 56 and out of a spray head 57. However, it is to be appreciated that any other suitable means for supplying volatised aromatic hydrocarbon to the airstream may be used.

The air decontamination device can be solely powered by mains electricity, solely powered by battery packs, which may be rechargeable, or may be selectively energisable by both power sources.

The air decontamination device can be produced in the form of a portable device, and this can take the dimensions of or substantially of a small briefcase. Alternatively, the air decontamination device can be produced as a larger device intended to remain in one location once installed. The latter device is more suitable for, but not limited to, industrial or commercial installations and premises.

In use, the air decontamination device is positioned in the location to be decontaminated. The device is intended to decontaminate air within a building, chamber, enclosure, trunking, pipe, channel or other enclosed or substantially enclosed area. However, with sufficient through-flow capacity, it can also decontaminate air in an open outside environment.

The device is energised, and the fan 20 generates a stream of ambient air along the passage 2 of the housing 1, as indicated by the arrows in FIG. 1. The air stream initially encounters the anode 31, dielectric 32 and cathode 33 which form the non-thermal plasma filter 30. The filter utilises the characteristics of a non-thermal plasma to 'plasmalyse' the constituent parts of the air within the dielectric core. In general terms, the outer ring electrons in the atomic structure of the elements comprising air (principally oxygen and nitrogen) are 'excited' by the intense electronic field generated by the non-thermal plasma, typically being 10 Kv at 20 KHz. The energised electrons release energy through collisions. However, little or no heat is emitted due to the insubstantial mass of the electrons and the consequent lack of ionisation that occurs. The released energy is sufficient to generated free radicals within the air stream, such as O. and $OH^-$. The free radicals are powerful oxidants, and will oxidise hydrocarbons, organic gases, and particles typically PM 2.5 ($2.5 \times 10^{-6}$ meters) and below, such as bacteria, viruses, spores, yeast moulds and odours. Only the most inert elements or compounds will generally resist oxidation.

Since many of the resultants of the oxidative reactions are transient and surface acting, due to having zero vapour pressure, by providing a molecular thick catalytic coating on some or all of the dielectric material of the non-thermal plasma, oxidation of particular molecules or compounds, for example nerve gas agents, within the non-thermal plasma can be targeted.

The non-thermal plasma filter 30 produces ozone as one of the by-products. The half-life of ozone is dependent on atmospheric conditions and, itself being a powerful oxidant, under normal circumstances will continue to react in the air long after it has exited the plasma core. This is unacceptable for a device operated by and in the general vicinity of people. Therefore, the Faraday cage formed by the cathode of the plasma filter houses a UV light emitting tube 40 surrounded by a mesh of an ozone-catalysing device 42. The mercury within the UV light emitting tube is excited by microwaves generated in the Megahertz frequency by the magnetron 62 of fixed or variable output. The ultraviolet radiation is emitted with peaks typically at 254 and 313 nanometers wavelength which act to break down the ozone entrained in the air stream. The coating on the mesh 42 acts to catalyse this break down. The use of microwaves to excite the UV light removes the need for separate circuitry to power the UV tube thereby reducing component complexity and numbers.

The microwaves also serve to excite the water molecules which exist in the emissions from the plasma cell due to the oxidation of hydrocarbons which will also benefit the efficiency of the plasma cell. This requires the mesh of the cathode component 33 to be wide enough to allow microwave energy to pass through the cage, to enter the plasma cell. Furthermore, it is widely known that microwaves in this frequency increase the intensity of non-thermal plasma fields, thereby serving to increase the overall efficiency of the device.

The (optional) introduction of a deionised water mist 75 from the reservoir 72 is sufficient to increase the relative humidity of the air passing through the device to >90%. This serves to increase the yield of hydroxyl radicals (OH.) and reduce the level of free ozone and oxides of nitrogen (NOx) in the emissions from the plasma cell. The deionised water should have a resistance of or about 18.2 MΩ/cm. Increasing the population of OH. free radicals at this stage of the process increases the efficiency of the subsequent stages early in the reaction's kinetic pathway, thus reducing the need for ozone in the air emitted by the process.

The dual function Faraday cage/reaction chamber also incorporates supports 90 for the UV emitting tube 40. These supports are coated with a material that catalyses the breakdown of ozone with water molecules into OH. free radicals and further are shaped to induce a swirl or rotation to the air passing through the chamber. A suitable coating material is Anatase form of titanium dioxide. It is preferable for all internal surfaces 11 to be similarly coated.

This destruction (photo-oxidation) of the ozone increases the free radical level, and particularly the level of Hydroxyl radicals $OH^-$, within the air stream. These free radicals also vigorously oxidise contaminants remaining within the air stream.

Trials have shown that free radicals resident in the air stream post-plasma filtering significantly increase the rate of generation of hydroxyl radicals during the photo-oxidative process.

The treated air that has passed through the reaction chamber and is emitted from the mesh 33 is rich in OH. radicals and contains a small amount of ozone, typically <100 ppb, and water vapour. In order to ensure that no significant ozone enters the chamber to be treated, the exhaust air is mixed with a measured volume of a hydrocarbon introduced by the spray head 57. The hydrocarbon is preferably a terpene, typically myrcene, which has no known toxicity. The unsaturated double bonds in the terpene molecule react preferentially with ozone, yielding more OH. radicals. This ozone-terpene reaction takes place within the device of the present invention, so that only the reactant products which in turn generate OH. radicals are emitted into the chamber/enclosure to be treated. The rate of rotation of the stepper motor 53 of the hydrocarbon emitter 50 governs the rate of delivery of the terpene. By linking the stepper motor to a control panel (not shown) the rate of terpene delivery can be precisely controlled thereby ensuring that the mass of free ozone in the exhaust is reacted with the appropriate mass of terpene. The air stream resulting from these reactions contains a cascade reaction known as "Open Air factor" which mimics a natural process in outdoor air which is responsible for the continuous decontamination of outdoor air.

The products of these preferential reactions have zero vapour pressure, and hence condense on any remaining particle in the air stream or surface. As a result, once the decontaminated air stream exits through the outlet 6 of the housing 1, decontamination of contaminants within the ambient air, and less quickly, on surfaces occurs.

These initiated condensation reactions outside of the decontamination device may cause small particulate 'growing', resulting, in extreme cases, in a visible fog or mist. This is undesirable. However, due to the air decontamination device effectively recirculating and re-decontaminating air within an environment, these small particulates are in any event removed within the non-thermal plasma filter 22.

The small particulates are actually beneficial in that they fuel the production of hydroxyl radicals within the plasma filter 30 once recirculated. Thus, although the potential for a visible fog is undesirable, it is beneficial in increasing the efficiency of the decontamination device, and thus the resultant safety of the ambient air.

The power supply for the device preferably incorporates a feedback circuit which enables the non-thermal plasma cell to operate at the optimum resonant frequency for that plasma cell under varying environmental conditions. It has been observed in experimentation that the resonant frequency of the cell and its capacitance vary considerably when the components of the air passing through the cell themselves vary from the norm. Thus enabling the power supply to constantly match the varying resonance will ensure optimum efficiency.

Furthermore, the power supply preferably incorporates a detector circuit (not shown) which monitors changes in capacitance and resonant frequency. The signal from this circuit may require amplification. The signal may be used to drive an indicator which will signal to an operator that the air component conditions have changed, for example, to provide warning of a gas or biological attack. This signal may also be used to operate a switch to engage multiple or duplicated components located within the device thereby providing an increased decontamination effort in response to an increased challenge.

The air stream generator can be driven in reverse, enabling decontamination of the interior of the device by drawing excess free radicals entrained in the air stream back through the device. As such, the device is largely self-cleaning.

Figure 3:
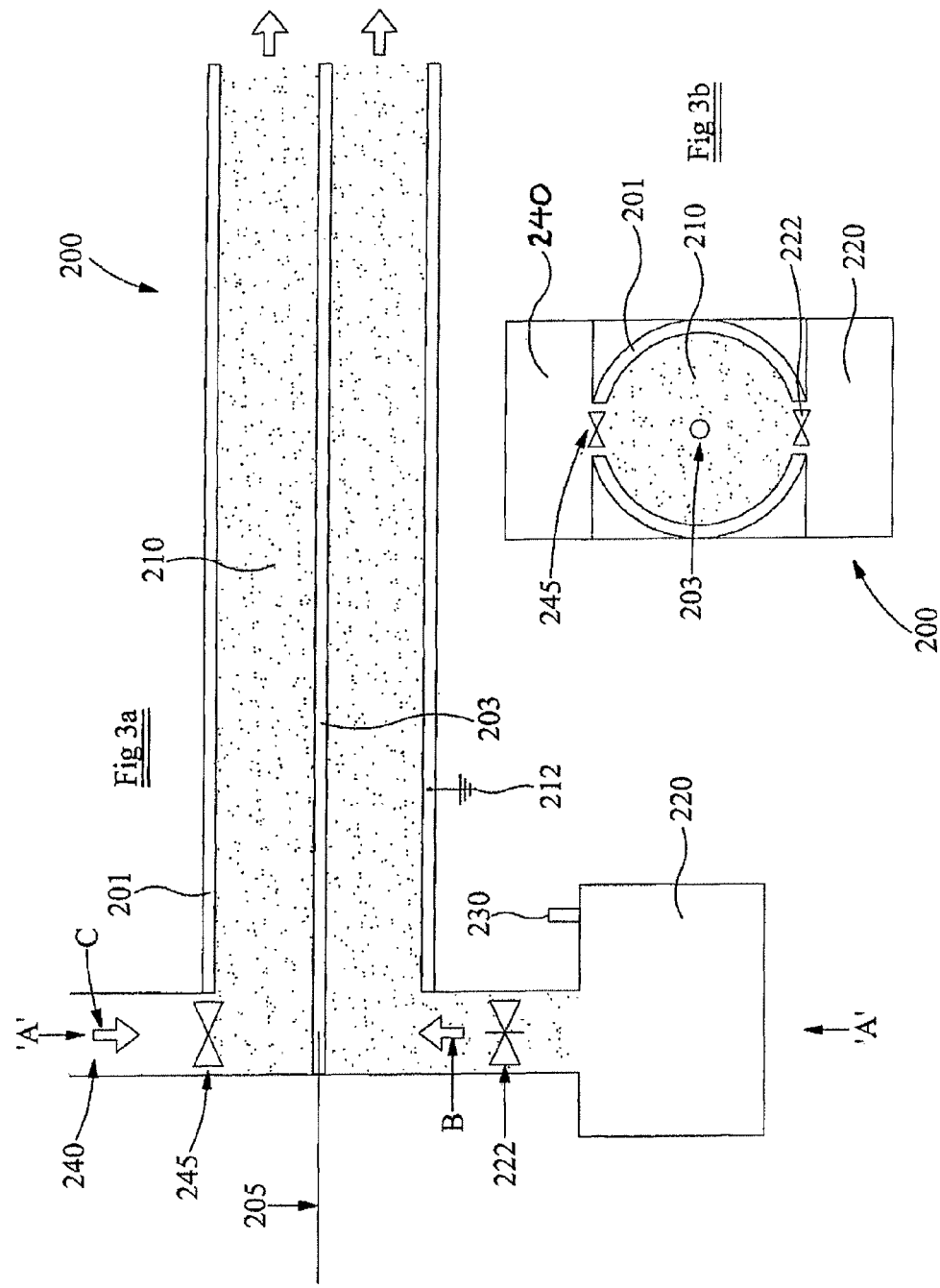

FIGS. 3a and 3b of the accompanying drawings illustrate an alternative aspect of the present invention wherein the dielectric of the plasma cell is replaced with a fine mist of de-ionised water. This embodiment minimises back pressure on the air delivery system reducing energy requirements and noise. Furthermore the presence of water droplets in the non-thermal plasma dramatically increase the yield of OH. radicals, as well as reducing ozone levels by increasing hydrogen peroxide levels and peroxone (or peroxozone) over the more traditional "dielectric sandwich" plasma design previously employed.

In further detail, the plasma cell 200 comprises a tubular component 201 wherein the wall of the tube serves as the cathode, the tube having a centrally fixed anode 203 connected to a high voltage/high frequency power supply 205 necessary to create a non-thermal plasma in the dielectric space 210 provided between the anode and the cathode. The cathode is earthed 212.

The dielectric in the dielectric space 210 is provided by a fine mist of deionised water. The water droplets should be small enough to float freely in the air and this may be achieved by using, for example, a proprietary ultrasonic atomiser provided in a reservoir 220. A fan 222 drives the de-ionised water vapour from the reservoir into the dielectric space 210 and an air inlet 230 supplies feed air into the reservoir where it is saturated with the water mist and propelled B into the tubular plasma cell 200. Air C from the surrounding environment (i.e. a room or chamber to be decontaminated) is introduced via a separate inlet 240 and propelled into the dielectric space by fan 245.

The control of the relative speeds of the fans 222, 245 enables the control and adjustment of the population of de-ionised water droplets in the dielectric space.

Figure 4:
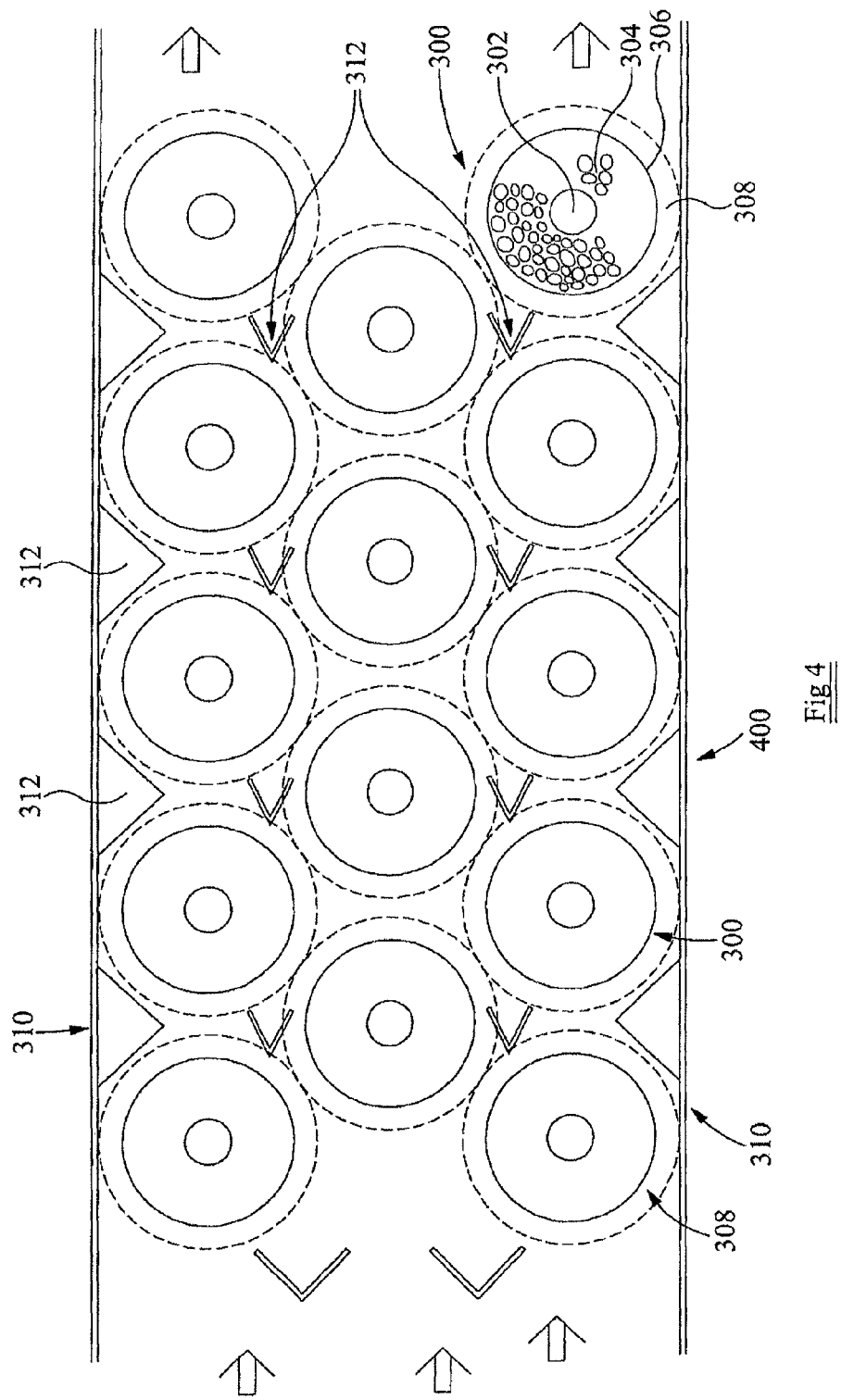
FIG. 4 is a longitudinal cross-sectional top view of an array of non-thermal plasma cells according to yet another aspect of the present invention.
Figure 5:
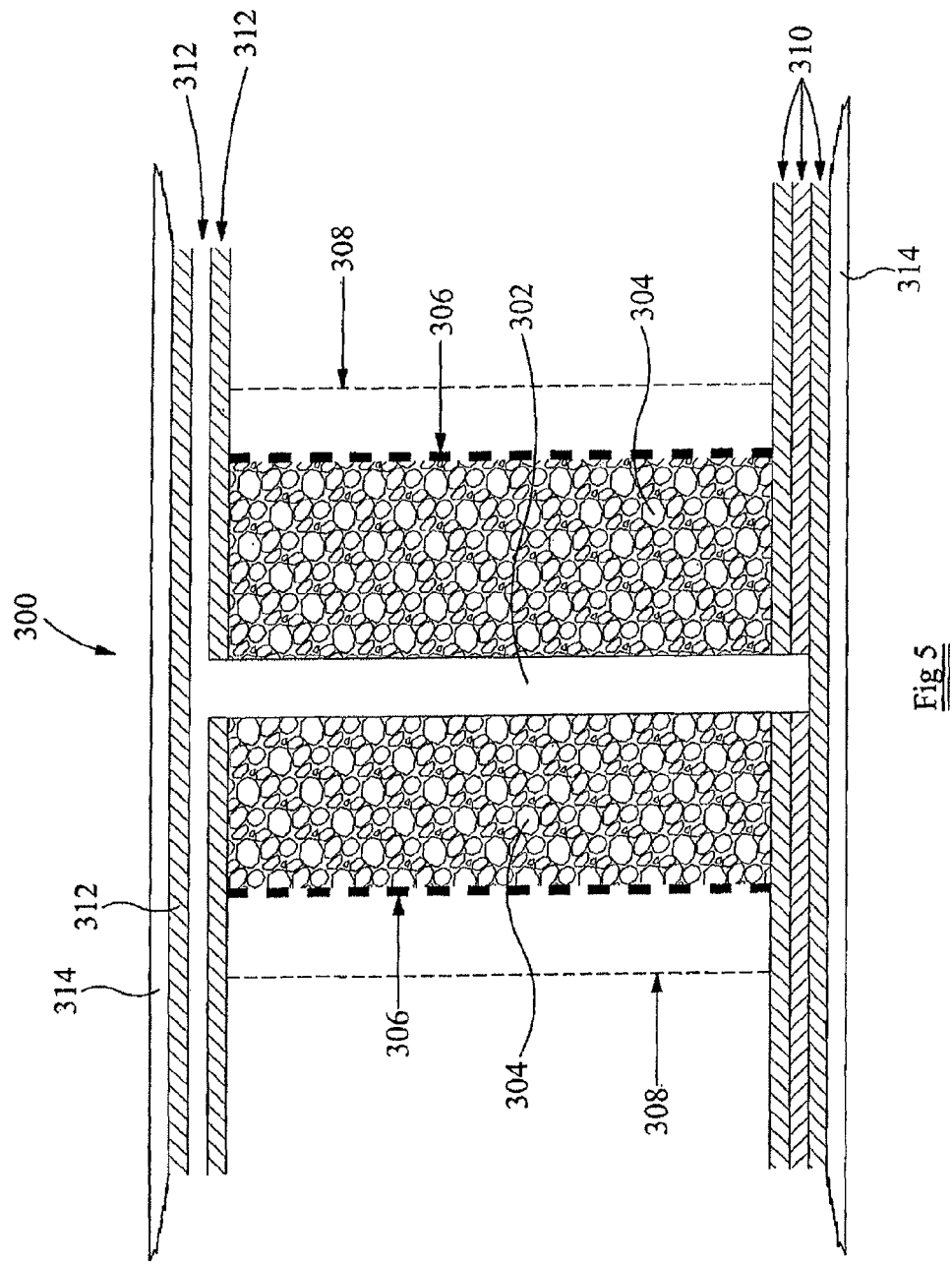
FIG. 5 is a vertical cross-section through a single plasma cell for the array shown in FIG. 4.
Figure 6:
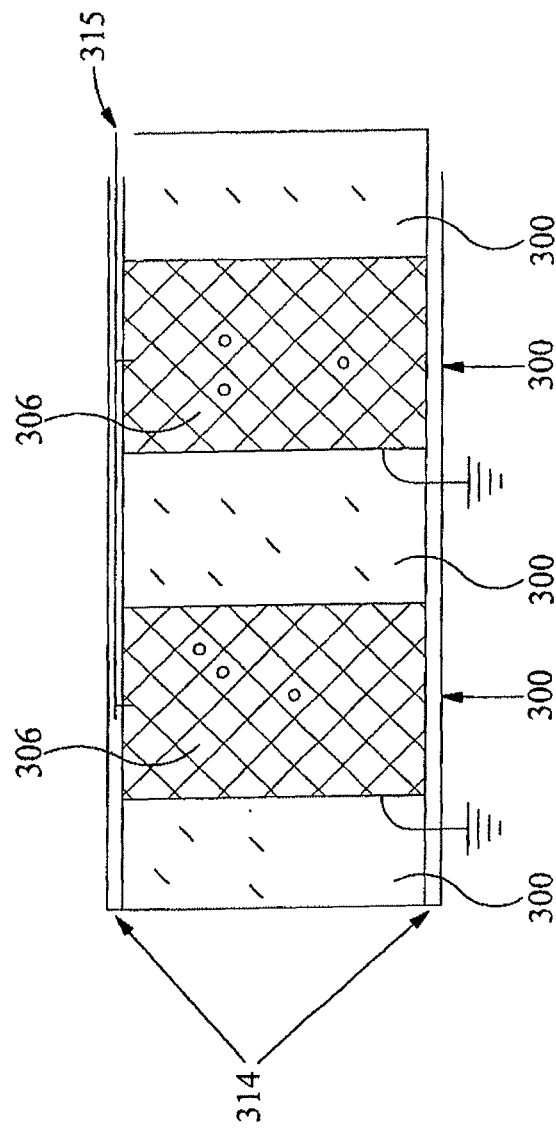
FIG. 6 is a schematic partial end view of the array of non-thermal plasma cells shown in FIG. 4.

FIGS. 4 to 6 of the accompanying drawings illustrate an alternative plasma cell 300, and an array of such cells 400, according another aspect of the present invention. Each plasma cell 300 of an array 400 is columnar and has a central high-voltage, high-frequency electrode 302 surrounded by a dielectric of activated alumina pellets 304, typically 5-6 mm in diameter. The activated alumina pellets are held in position relative to the central anode by means of a cathode mesh 306, of a size suitable to retain the pellets. When a suitable power supply 315, typically 10 Kv at 20 KHz is applied to the electrodes, a non-thermal plasma is created in the dielectric 304 between the anode 302 and cathode 306. It has been demonstrated by experimentation that the effective non-thermal plasma field 308 (illustrated by broken lines in FIGS. 4 and 5) extends some way beyond the physical size of the cell, probably due to electrons freed by the energy created within the cell.

The arrangement of the individual columnar cells in staggered rows, as shown in FIG. 4, makes use of the "extended" plasma field 308 to treat air (represented by the arrows in FIG. 4) that is directed through the array whilst minimising back pressure within the decontamination system. Again, this provides a more efficient and economical device. Each outer wall of the array is provided with insulation, for example in the form of a laminated structure 310, for example of silicone rubber, as shown in FIG. 5.

Additionally, baffles 312 are provided on the internal the wall of the array 400 and between rows of the cells to guide air between the individual plasma cells 300. The plasma fields 308 touch or overlap (depending upon the spacing of the cells and field applied) and thus the air cannot pass through the array without entering a plasma state. The physical control of the air directs the air stream at the plasma columns, ensuring larger particles and molecules are adsorbed partially on to the dielectric material 304, allowing a longer exposure to the plasma field 308, and the inherent oxidative action, that acts to destroy these larger contaminants.

The individual cells making up the array may be sequentially switched at a frequency sufficient to maintain a non-thermal plasma in the individual cells, even though the power supplying that cell is momentarily absent. This relies on the observation that a pulsed non-thermal plasma state exists for several hundredths of second longer than the pulse of electrical energy required to create it. Such sequential switching may be obtained by using proprietary automotive distribution technology, electro-mechanical or solid-state.

The embodiments described above are given by way of example only, and modifications will be apparent to persons skilled in the art without departing from the scope of the invention as defined by the appended claims.

The invention claimed is:

1. An apparatus for decontamination of air, the apparatus comprising:
   a housing having an air inlet and an air outlet with an air passage therebetween;
   an arrangement adapted to direct a stream of air through the housing; and
   a non-thermal plasma cell, an ultraviolet (UV) emitting device and an ozone depletion catalyst all included in the housing, the non-thermal plasma cell comprising an anode, a dielectric and a cathode, the cathode being a meshed enclosure which surrounds the ultraviolet emitting device and ozone depletion catalyst to form a reaction chamber and Faraday cage,
   wherein the dielectric comprises deionized water droplets or vapor.

2. An apparatus for decontamination of air, the apparatus comprising:
   a housing having an air inlet and an air outlet with an air passage therebetween;
   an arrangement adapted to direct a stream of air through the housing;
   a non-thermal plasma cell, an ultraviolet (UV) emitting device and an ozone depletion catalyst all included in the housing, the non-thermal plasma cell comprising an anode, a dielectric and a cathode, the cathode being a meshed enclosure which surrounds the ultraviolet emitting device and ozone depletion catalyst to form a reaction chamber and Faraday cage; and a water droplet emitter provided within the housing to deliver a fine spray of water into the reaction chamber.

3. An apparatus for decontamination of air, the apparatus comprising:

a housing having an air inlet and an air outlet with an air passage therebetween, an arrangement adapted to direct a stream of air through the housing, and a non-thermal plasma cell, an ultraviolet (UV) emitting device and an ozone depletion catalyst all included in the housing, the non-thermal plasma cell comprising an anode, a dielectric and a cathode, the cathode being a meshed enclosure which surrounds the ultraviolet emitting device and ozone depletion catalyst to form a reaction chamber and Faraday cage, wherein the housing includes an arrangement adapted to deliver microwaves of a certain wavelength to the reaction chamber.

4. The apparatus of claim 3 further comprising a hydrocarbon emitter provided within the housing downstream of the reaction chamber.

5. The apparatus of claim 3 wherein the cathode comprises a porous mesh of conducting material that is formed into a cage-like structure for surrounding the UV emitting device and ozone depletion catalyst.

6. The apparatus of claim 3 wherein the ozone depletion catalyst surrounds the UV emitting device.

7. An apparatus for decontamination of air, the apparatus comprising:

a housing having an air inlet and an air outlet with an air passage therebetween;

an arrangement adapted to direct a stream of air through the housing; and a non-thermal plasma cell, an ultraviolet (UV) emitting device and an ozone depletion catalyst all included in the housing, the non-thermal plasma cell comprising an anode, a dielectric and a cathode, the cathode being a meshed enclosure which surrounds the ultraviolet emitting device and ozone depletion catalyst to form a reaction chamber and Faraday cage, wherein the cathode houses a microwave emitter for delivering microwaves of a certain wavelength to excite the UV emitting device.

\* \* \* \* \*